United States Patent
Lou et al.

(10) Patent No.: US 10,079,072 B2
(45) Date of Patent: Sep. 18, 2018

(54) BIOLOGICALLY INSPIRED INTELLIGENT BODY SCANNER

(71) Applicant: Siemens Healthcare GmbH, Erlangen (DE)

(72) Inventors: Bin Lou, West Windsor, NJ (US); Dorin Comaniciu, Princeton Junction, NJ (US)

(73) Assignee: Siemens Healthcare GmbH, Erlangen (DE)

( * ) Notice: Subject to any disclaimer, the term of this patent is extended or adjusted under 35 U.S.C. 154(b) by 9 days.

(21) Appl. No.: 15/385,691

(22) Filed: Dec. 20, 2016

(65) Prior Publication Data
US 2018/0173852 A1 Jun. 21, 2018

(51) Int. Cl.
- G06K 9/00 (2006.01)
- G16H 40/40 (2018.01)
- G06T 7/00 (2017.01)
- G16H 50/20 (2018.01)
- A61B 6/03 (2006.01)
- A61B 6/00 (2006.01)
- G16H 40/63 (2018.01)

(52) U.S. Cl.
CPC ........... *G16H 40/40* (2018.01); *A61B 6/032* (2013.01); *A61B 6/545* (2013.01); *G06T 7/0012* (2013.01); *G16H 40/63* (2018.01); *G16H 50/20* (2018.01); *G06T 2207/10088* (2013.01); *G06T 2207/20081* (2013.01); *G06T 2207/20084* (2013.01)

(58) Field of Classification Search
None
See application file for complete search history.

(56) References Cited

U.S. PATENT DOCUMENTS

| | | | | |
|---|---|---|---|---|
| 8,538,109 B2 * | 9/2013 | Vitanovski | ........... | G06K 9/4638 382/128 |
| 9,245,091 B2 * | 1/2016 | Voigt | .................... | G06F 19/321 |
| 9,918,690 B2 * | 3/2018 | Itu | ........................ | A61B 6/5217 |

(Continued)

OTHER PUBLICATIONS

Extended European Search Report (EESR) dated May 22, 2018 in corresponding European Patent Application No. 17208028.5.
(Continued)

*Primary Examiner* — Shervin Nakhjavan

(57) ABSTRACT

An intelligent medical imaging scanner system includes an image scanner, an operator interface, a database, processors, and a storage medium. The database includes a learning model for relating configurations of the image scanner to operator input requirements. The storage medium contains programming instructions that, when executed, cause the processors to determine whether the learning model may be used to generate a configuration of the image scanner corresponding to the new input requirements. If the configuration can be generated, the processors use that configuration to acquire images of a patient using the image scanner. If the configuration of the image scanner cannot be generated, the processors perform an accommodation process comprising (a) modifying the learning model to generate a new configuration of the image scanner corresponding to the new input requirements, and (b) using the new configuration to acquire the images of the patient using the image scanner.

19 Claims, 4 Drawing Sheets

(56) References Cited

U.S. PATENT DOCUMENTS

2004/0264628 A1* 12/2004 Besson .............. A61B 6/032
378/5
2011/0299747 A1   12/2011 Solf et al.
2012/0232386 A1*  9/2012 Mansi .............. A61B 8/0883
600/437
2015/0085971 A1   3/2015 Braun et al.
2016/0364527 A1* 12/2016 Reicher ............ G06N 99/005

OTHER PUBLICATIONS

Ghat, et al; "Automatic selection of radiological protocols using machine learning"; Proceedings of the 2011 Workshop on Data Mining for Medicine and Healthcare, DMMH 111, Jan. 1, 2011; New York, New York, USA; p. 52.

Wang, et al; "Machine learning and radiology", Medical Image Analysis, Oxford University Press, Oxford, GB, vol. 16, No. 5, Feb. 12, 2012 (Feb. 12, 2012), pp. 933-951;12): pp. 933-951.

Tommasino, et al.; "Reinforcement learning algorithms that assimilate and acconmodate skills with mul tiple tasks"; Developm Ent and Learning and Epigenetic Robotics (ICDL), 2012 IEEE International Conference On, IEEE, Nov. 7, 2012 (Nov. 7, 2012), pp. 1-8.

* cited by examiner

BIOLOGICALLY INSPIRED INTELLIGENT BODY SCANNER

TECHNICAL FIELD

The present invention relates generally to methods, systems, and apparatuses associated with a medical scanner that employs a biologically inspired scanning procedure. The disclosed methods, systems, and apparatuses may be applied to scanners for any imaging modality.

BACKGROUND

In conventional medical imaging examinations, the protocols of diagnostic scans are usually defined in an initial planning phase. Radiologists then interpret acquired images and send reports to the referring physicians for further diagnosis. There are two major issues within this workflow. First, there is a gap between diagnostic requirements and actual input/output of the scanners. The quality of the scan ultimately depends to a large degree on the expertise of the operator. If the operator lacks expertise, the measurements might not be taken accurately enough to provide sufficient information for a successful diagnosis. The second issue with the workflow is that, although all scanners have a large amount of pre-installed standard protocols and algorithms, these protocols and algorithms are generally not robust enough to apply to all conditions under which scanning is performed. Moreover, it is difficult for the operator/radiologists to adjust settings or search for optimal solutions when facing new requirements.

To address the aforementioned deficiencies, intelligent scanners have been proposed that focus on leveraging post-processing techniques to augment image quality or imaging speed. For example, image fusion techniques in ultrasound can stitch images together and generate larger field-of-view of a target object; registration algorithms can identify the mid-sagittal plane the brain from MR scans and provide consistent geometry of diagnostic scans; motion correction approaches can improve the visualization of the heart by reducing the impact from cardiac motion. However, these developments still highly rely on the expertise of operators to determine protocols and organize workflows. The inputs to the scanners are either rather general, e.g. a fast preliminary scan for all purposes, or dedicated to certain disease/patient, e.g. complex settings designed to image the disease. Modern image scanners are essentially a combination of the conventional image scanning and an additional imaging analyzer.

Accordingly, it is desired to provide a scanning system that does not impose restrictions on providing customized scans for different types of diagnostic requirements, while also not overly relying on the expertise of operators.

SUMMARY

Embodiments of the present invention address and overcome one or more of the above shortcomings and drawbacks, by providing methods, systems, and apparatuses related to a biologically inspired human body scanner.

According to some embodiments of the present invention, an intelligent medical imaging scanner system includes an image scanner, an operator interface, a database, one or more processors, and a non-transitory, computer-readable storage medium in operable communication with the one or more processors. The operator interface is configured to receive operator input. The database includes a learning model for relating configurations of the image scanner to operator input requirements. The computer-readable storage medium contains one or more programming instructions that, when executed, cause the processors to, in response to receiving of new input requirements via the operator interface, determining whether the learning model may be used to generate a configuration of the image scanner corresponding to the new input requirements. If the configuration of the image scanner can be generated based on the new input requirements, the processors use the configuration to acquire one or more images of a patient using the image scanner. If the configuration of the image scanner cannot be generated based on the new input requirements, the processors perform an accommodation process comprising (a) modifying the learning model to generate a new configuration of the image scanner corresponding to the new input requirements, and (b) using the new configuration to acquire the one or more images of the patient using the image scanner.

Various refinements, enhancements, or other modifications may be made to the aforementioned system in different embodiments of the present invention. For example, in some embodiments, the processors use natural language processing to derive input parameters for the learning model based on the new input requirements received via the operator interface. Then, the processors apply a feature extraction model to refine the input parameters for the learning model based on the new input requirements. In other embodiments, the processors may be used to predict a disease outcome based on the one or more images. In some embodiments, the learning model is modified during the accommodation process based on operator or patient feedback to acquisition of the one or more images by the image scanner.

In some embodiments of the aforementioned system, a workflow for the image scanner is derived based on the new configuration of the image scanner. The operator interface may be configured to receive operator feedback related to the workflow for the image scanner and wherein the learning model is modified based on the operator feedback. This operator feedback may include, for example, a modification to the workflow automatically detected by the intelligent medical imaging scanner system while an operator is performing the workflow.

According to another aspect of the present invention, a computer-implemented method for performing medical image acquisition includes determining whether one or more learning models may be used to generate a configuration of the image scanner corresponding to the input requirements received via an operator interface of an image scanner. This configuration may include, for example, recommended acquisition parameters, recommended workflow, recommended image processing parameters, and recommended image processing algorithms. If the configuration of the image scanner can be generated based on the input requirements, the configuration is generated with the learning models based on the input requirements. If the configuration of the image scanner cannot be determined based on the input requirements, the learning models are modified to generate the configuration of the image scanner corresponding to the input requirements. Then, the configuration is applied to acquire one or more images of a patient using the image scanner. In some embodiments, the method further includes using natural language processing to extract scanner-related features from the input requirements these scanner-related features may be used by learning models in deriving the configuration.

The learning models used in the aforementioned method may generally be any type of learning model known in the art including, without limitation, deep learning artificial neural networks. In some embodiments, the method further includes receiving feedback comprising an operator modification to the recommended acquisition parameters, the recommended workflow, and the recommended image processing parameters, or the recommended image processing algorithms. Then, the learning models may be modified based on the feedback. In one embodiment, three different models are used by the method a first model configured to derive the recommended acquisition parameters based on the input requirements, a second model configured to derive the recommended workflow based on the input requirements, and a third model configured to derive the recommended image processing parameters and the recommended image processing algorithms based on the input requirements. In response to receiving first feedback comprising an operator modification to the recommended acquisition parameters, the first model may be modified accordingly. Additionally, the second model may be configured to derive the recommended workflow based on the input requirements as modified in the first feedback. The second model may also be modified based on second feedback comprising an operator modification to the recommended workflow. The first and second feedback may also be used by the third model to derive the recommended image processing parameters and the recommended image processing algorithms. Additionally, the third model may be modified based on third feedback comprising an operator modification to the recommended workflow; and According to other embodiments of the present invention, a computer-implemented method for configuring an intelligent medical scanner includes receiving input requirements corresponding to a medical imaging scan of a patient and processing the input requirements with a learning model to determine whether a pre-existing configuration of the intelligent medical scanner exists which is compatible with the input requirements. If the pre-existing configuration does not exist, operator feedback is collected corresponding to one or more previous image acquisitions performed using the intelligent medical scanner. Then, the learning model is modified based on the operator feedback to generate a new configuration based on the input requirements.

Additional features and advantages of the invention will be made apparent from the following detailed description of illustrative embodiments that proceeds with reference to the accompanying drawings.

BRIEF DESCRIPTION OF THE DRAWINGS

The foregoing and other aspects of the present invention are best understood from the following detailed description when read in connection with the accompanying drawings. For the purpose of illustrating the invention, there are shown in the drawings embodiments that are presently preferred, it being understood, however, that the invention is not limited to the specific instrumentalities disclosed. Included in the drawings are the following Figures.

DETAILED DESCRIPTION

Systems, methods, and apparatuses are described herein which relate generally to various techniques related to a biologically inspired human body scanner. Artificial intelligence is being used in more and more fields and it has been proved successful in the healthcare industry. Various smart systems have been developed to assist doctors in the effort to provide safer, faster and more accurate examinations. With respect to the medical imaging devices, it is essential to enable scanners to increase capabilities of dealing with new problems, or solving optimally the existing problems. The techniques described herein provide an innovative design of intelligent scanner that imitates the model of human intellectual development, especially including the ability to learn from past experiences. The performance of the scanner can be significantly augmented through learning and training from its previous scans without specialist intervention. The techniques described herein may generally be applied to any imaging modality.

Briefly, the techniques describe herein apply concepts in the intellectual development model of Swiss psychologist Jean Piaget to operation of medical imaging scanner. In Piaget's theory people organized knowledge into "schemas." Each schema tells an individual how to react to incoming information. A process referred to as "assimilation" allows an existing schema to deal with a new object or situation. When an existing schema does not address the object or situation, the schema is modified through a process referred to as "accommodation." With the techniques described herein, the "schema" of the scanner is how it organizes various components organizing all components (functional modules, protocols, etc.) for a scan requirement. The capability of scanner grows as a process of adaptation (adjustment) to the input requirements. When receiving new scanning requirements, the scanner determines whether using an existing schema can be used in selecting the applicable components for performing the scan. If yes, then the knowledge of the existing schema (e.g. protocols, parameters) is applied to perform the scan. This is akin to assimilation, as defined in Piaget's theory. The accommodation process occurs when the existing schema does not work, and needs to be changed to deal with a new scanning requirement. This drives a learning process that updates the schema based on feedback from various sources.

Figure 1:
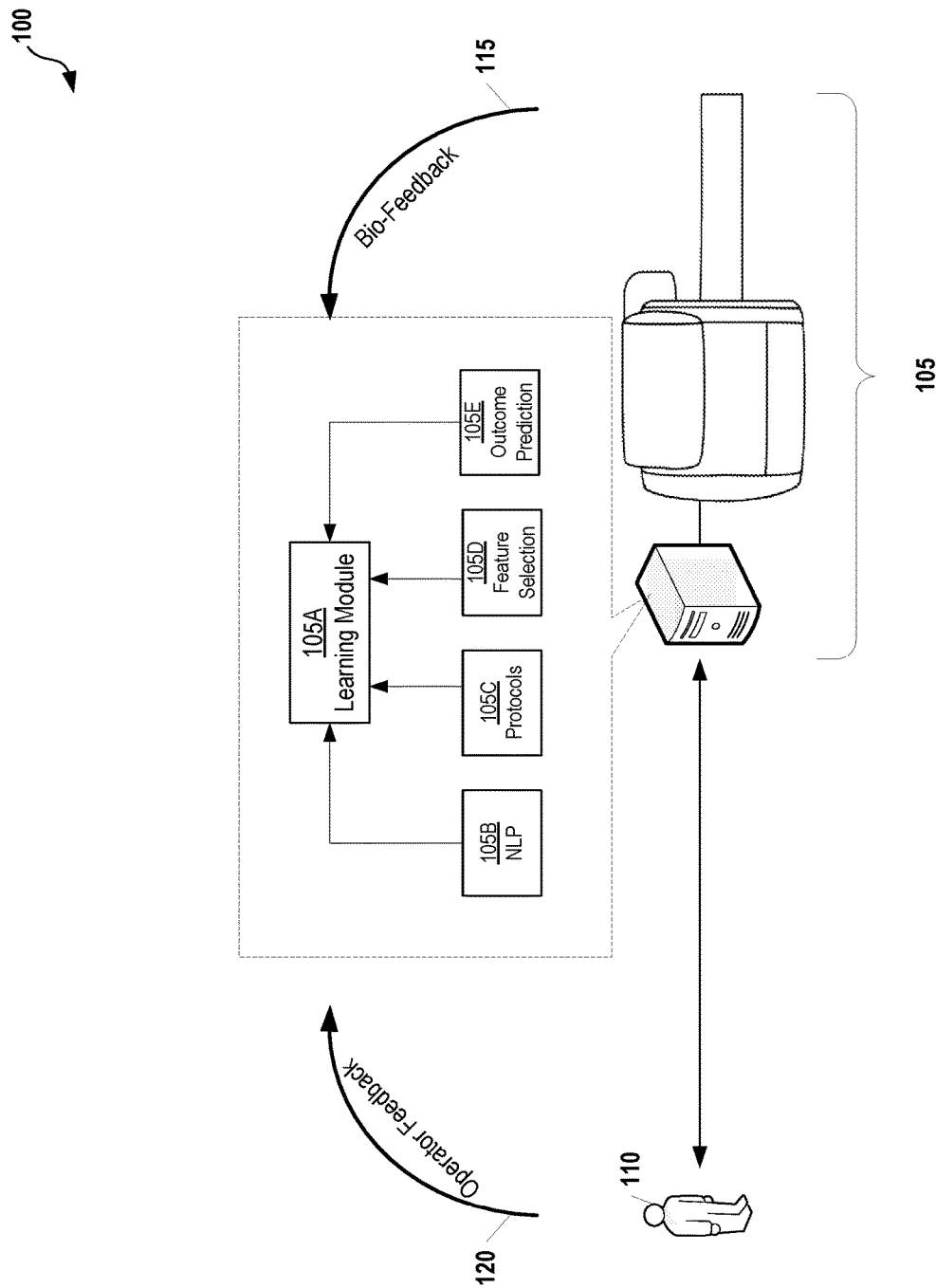
FIG. 1 provides a high-level view of a system which illustrates how an Intelligent Medical Imaging Scanner may be applied to perform medical image acquisition.

FIG. 1 provides a high-level view of a system 100 which illustrates how an Intelligent Medical Imaging Scanner 105 may be applied to perform medical image acquisition, according to some embodiments. Briefly, the system 100 includes an Intelligent Medical Imaging Scanner 105 operated by an Operator 110. The Intelligent Medical Imaging Scanner 105 provides an operator interface (not shown in FIG. 1) through which the Intelligent Medical Imaging Scanner 105 can receive input requirements from the Operator 110 and present information related to the scanning procedure. The Intelligent Medical Imaging Scanner 105 includes a group of processing modules 105A, 105B, 105C, 105D, and 105E. Each individual module may itself be an application that executable by the processors on the Intelligent Medical Imaging Scanner 105. Alternatively, various modules can be combined in one or more executable applications. In the example of FIG. 1, the scanner is a magnetic resonance imaging (MRI) scanner however, in principle, any type of image scanner may be used (e.g., Computed Tomography, etc.).

The Learning Module 105A of the Intelligent Medical Imaging Scanner 105 is designed to operate in a manner that is similar to the human intellectual development model proposed by Piaget. In Piaget's theory, the intellectual development of children derives from two cognitive processes, named assimilation and accommodation. Children use these two processes to create a mental framework to perceive and interpret what they experience from external world. In this context, "assimilation" means incorporating new information into an already existing cognitive framework. This existing framework is called a "schema," which is a structured cluster of concepts that is created when children interact with their physical and social environments. For example, if a child knows how to solve problems of the sum of two numbers, the child already obtained a cognitive structure for calculating sum problems and thus is capable of solving similar problems by incorporating new information into the existing structure. The second process of intelligence development, "accommodation," means a child either modifies an existing framework or forms an entirely new framework into which new information can be incorporated. For example, when a child is asked to learn how to solve multiplication problems that were never dealt with before, the accommodation process is then involved to deal with a new object or event.

This intellectual development model provides a basic idea for the system design of intelligent scanner, which can learn and optimize scanning procedures for any special diagnostic requirement. To achieve this goal, the first step is to have the intelligent scanner mimic the "assimilation" process, which means incorporating new information into an already existing framework. The analogy of the cognitive schema in our intelligent scanning system is the hardware/software architecture and functional modules of the Intelligent Medical Imaging Scanner 105. For example, suppose the Intelligent Medical Imaging Scanner 105 has a set of pre-defined Protocols 105C that may be utilized, parameter settings and post-processing algorithms. For an incoming scanning requirement from the Operator 110 to be achieved, the Medical Imaging Scanner 115 is able to fit the requirement into the current framework and select the most appropriate protocols, parameters, algorithms, workflows, etc.

The conventional scanning procedure is similar to "assimilation" but it needs human intervention to control the process. The scanner has a large amount of pre-defined protocols, parameters and image processing algorithms stored in it. In order to conduct successful scans, the conventional system needs operators to master particular measuring techniques and detailed knowledge of the specific application field. However, the Intelligent Medical Imaging Scanner 105, designed according to the techniques described herein, can perform successful measurements without human intervention or professional intuition/experience of experts. Therefore, the Intelligent Medical Imaging Scanner 105 includes a Feature Selection 105D module that uses advanced feature selection and extraction techniques to convert real-world requirements into representations under the scanner framework. After the conversion, input information from the Operator 110 can be incorporated into the scanner system framework to search for the optimized solution. The functionality of Feature Selection 105D module can be realized through various machine learning methods or deep learning networks.

Another extended question is how to precisely present practical requirements in the scanner system. The Intelligent Medical Imaging Scanner 105, according to some embodiments of the present invention, provides a problem-oriented user interface, as well as a function of interpretation of human language via a natural language processing (NLP) module 105B. Using the NLP module 105B, semantic information relative to scan requirements should be extracted and processed. NLP research has provided many solutions to link the semantic space and mathematical vector space, any of which may be applied to allow the Operator 110 to communicate with the Intelligent Medical Imaging Scanner 105 in a more natural manner. For example, the Operator 110 may provide information such as the type of scan being performed and the desired output image types. The Intelligent Medical Imaging Scanner 105 can use the NLP Module 105B to interpret this information and select from the pre-defined Protocols 105C to determine a set of parameters for performing the scan. Additional patient-specific information may be provided by the Operator 110 to further refine this process, such as demographic information, medical history, etc.

The realization of "assimilation" process may not be appropriate for the Intelligent Medical Imaging Scanner 105 to deal with new problems. A more important characteristic is the capability of learning and adapting when the environment changes. The analogy of "accommodation" is the learning procedure of the intelligent scanner when new scan requirements are sent to it. Compared to the conventional scanner, one significant improvement in the Intelligent Medical Imaging Scanner 105 is to use a real-time programmable architecture to replace the fixed architecture. This dynamic programmable architecture comprises both hardware and software systems. With the dynamic system, the Intelligent Medical Imaging Scanner 105 is able to update existing protocols and parameters for specific scan requirements, or even generating new protocols for new requirements. Machine learning techniques such as deep reinforcement learning architectures and models general known in the art may be used to achieve this goal (e.g., deep neural networks, deep belief networks, recurrent neural networks, etc.). Through a large amount of training (using both real data and simulated data), the Intelligent Medical Imaging Scanner 105 can realize functions that are challenging (or very difficult) for humans, such as: providing the optimized solution of radiation dosage, suggesting user work-flow of highest productivity, finding best field-of-view for a target object, etc. The ultimate goal is to select the best protocol, minimize the ionizing radiation (in the case of X-Ray or CT), avoid the incidence of costly rescans, and reduce the risk of incorrect diagnoses (these can be the target functions for training the model). Operator Feedback 120 such as modifications to newly generated protocols, workflows, and processing parameters may be used to further refine the Learning Module 105A.

According to Piaget's model, assimilation and accommodation do not work in isolation. The development of human intelligence represents a dynamic equilibrium between the above two processes. Consequently, the implementation of the Intelligent Medical Imaging Scanner 105 should allow new scans to run through both processes. One way to achieve this goal is via integrating probabilistic models and evaluation functions. The probabilistic model provides a confidence level of how much the new scan requirement can be fit into existing framework and the evaluation functions suggest quantitative measurement of the improvement after updating the system.

Another prominent characteristic of the Intelligent Medical Imaging Scanner 105 is the ability of interaction with external environments. The typical interaction is with the Operator 110 who can evaluate the scan results so the scanner uses the evaluation to improve its performance. However, the interaction can be not only with operators but also with the patients being scanned. In some embodiments, the Intelligent Medical Imaging Scanner 105 is configured to collect Bio-Feedback 115 from the patient, for example, using the collected imaging data or other bio-sensors (e.g., electrocardiogram). The Bio-Feedback 115 can be used to detect complex physiological parameters of the patients and accept more types of input information about their medical history. The Intelligent Medical Imaging Scanner 105 can then integrate all information to monitor the status of the patients during the scan and adjusts parameters accordingly.

Aside from managing the image acquisition process, the Intelligent Medical Imaging Scanner 105 may additionally be used in some embodiments for predicting disease outcome based on the Bio-Feedback 115. In the example of FIG. 1, the Intelligent Medical Imaging Scanner 105 has an Outcome Prediction 105E module which operates in conjunction with the Learning Module 105E to analyze the Bio-Feedback 115 and provide disease prediction. It should be noted that outcome prediction may be based, in some embodiments, on additional information besides the Bio-Feedback 115. For example, in some embodiments, the system can analyze the image just acquired to provide disease predictions or identify abnormality in the image (e.g., abnormal volume of an organ, deformation of an organ, etc.).

The contents of the Outcome Prediction 105E module can, in some embodiments, be one or more disease prediction models and an interface for interacting with other components of the Intelligent Medical Imaging Scanner 105 (e.g., to facilitate retrieval of the Bio-Feedback 115). In other embodiments, the models within the Learning Module 105A may be utilized. The prediction provided by the Outcome Prediction 105E can be used as an additional form of feedback for the Learning Module 105A. In this way, over time, the Learning Module 105A can learn how to derive acquisition parameters, workflows, and processing parameters that provide optimal conditions for disease prediction.

In some embodiments, a graphical user interface (GUI) is provided in the Intelligent Medical Imaging Scanner 105 or in an ancillary system to support communications at various levels. For example in some embodiments, the GUI includes a problem-oriented interface that is very general and user-friendly but has limit on the application of system facilities. This interface may relevant information such as description of patient's syndrome, medical history, and provisional diagnosis in a natural language format. The GUI may also include a lower-level interface which is similar to the interface provided on conventional medical imaging scanners. Thus, operators/technicians can determine the meaning of each specific parameter so they can customize the scanning according to their knowledge.

Figure 2A:
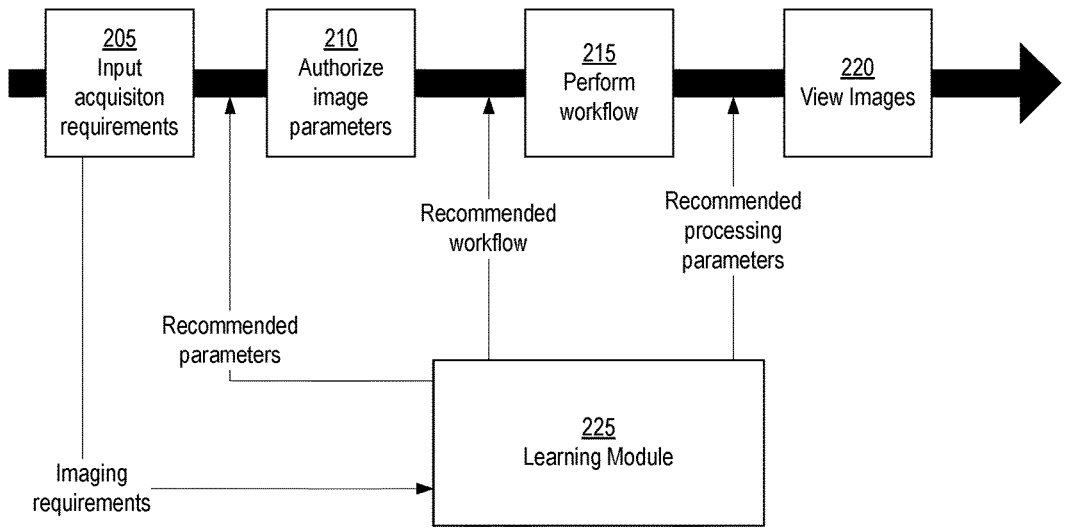
FIG. 2A provides an illustration of how the Learning Module used by an Intelligent Medical Imaging Scanner may be used in a typical imaging scenario, according to some embodiments.
Figure 2B:
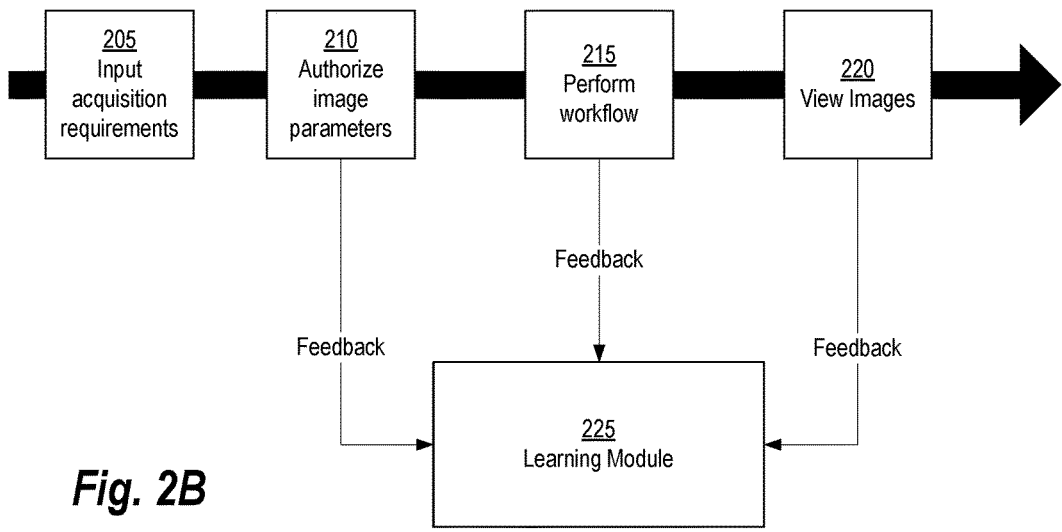
FIG. 2B provides an additional illustration of how the Learning Module used by an Intelligent Medical Imaging Scanner may be used in a typical imaging scenario, according to some embodiments.

FIGS. 2A and 2B illustrate how the Learning Module 225 used by an Intelligent Medical Imaging Scanner may be used in a typical imaging scenario. Briefly, the Learning Module 225 is used to generate recommended acquisition parameters, workflow, and processing parameters for performing the imaging scan. In principle, each of these items can be generated prior to performing the scan and modified, if necessary, by the operator. However, FIGS. 2A and 2B show an alternative process where the acquisition parameters, workflow, and processing parameters recommended by the Learning Module 225 are presented to the operator individually as the operator proceeds through four steps 205, 210, 215, and 220. Based on how the operator utilizes the recommended data, feedback is collected and used to refine the various models in the Learning Module 225.

FIG. 2A shows the flow of data between the operator interface and the Learning Module 225. Starting at step 205, the imaging requirements are input by the operator and sent to the Learning Module 225. The Learning Module 225 then generates a list of recommended parameters which are presented to the operator of the Intelligent Medical Imaging Scanner. Next, at step 210, the operator authorizes imaging parameters for performing the scan. These may be the parameters provided by the Learning Module 225 or (as described below with reference to FIG. 2B), these parameters may be modified versions of those provided by the Learning Module 225. Based on the parameters, the Learning Module 225 provides the operator which a recommended workflow. The term "workflow" here refers to one or more tasks to be performed by the operator, possibly in conjunction with the Intelligent Medical Imaging Scanner, to achieve the desired imaging data. For example, workflow tasks may include placement of the patient on the scanner table, safety procedures, etc. At step 215, the operator performs the workflow to acquire raw image data. The Learning Module 225 then suggests processing parameters which are used to transform the raw image data into viewable images. These processing parameters may include, for example, parameters used to perform image reconstruction. The images are then generated based on the processing parameters (with or with modification from the operator), before being viewed by the operator and/or radiologist at step 220.

FIG. 2B shows how feedback from the operator may be collected during steps 205, 210, 215, and 220. In general, any type of feedback may be collected. For example, at step 210, the feedback may be binary (i.e., did the operator accept or reject the recommended parameters) or it can comprise a list of modifications to the recommended parameters. Similar feedback can be collected with regards to the workflow and the processing parameters recommended by the Learning Module 225. Following step 220, where the images are viewed by the operator or radiologist, additional feedback may be collected such as whether the image provides the desired results. Again a binary system may be used (e.g., acceptance or rejection) or more feedback mechanisms may be used. For example, in some embodiments, the radiologist may provide a comment such as "too much contrast" which can be interpreted by the natural language functionality of the Intelligent Medical Imaging Scanner and used to further refine the learning model.

Figure 3:
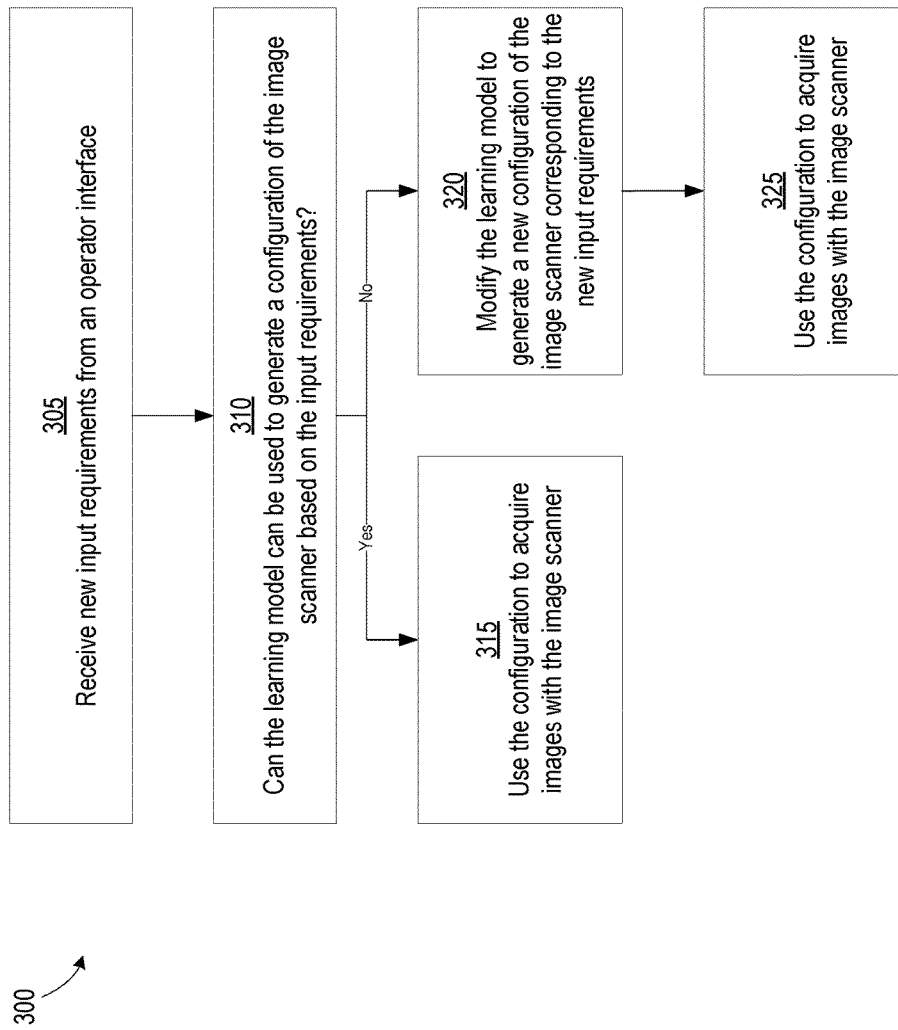
FIG. 3 illustrates an exemplary computing environment within which embodiments of the invention may be implemented.

FIG. 3 illustrates a process 300 for operating an intelligent medical imaging scanner system, according to some embodiments. For the purposes of this example, it may be assumed that the intelligent imaging scanner system includes an image scanner, an operator interface configured to receive operator input, one or more processors, and a database comprising a learning model for relating configurations of the image scanner to operator input requirements. The learning model in akin to the schema used in Piaget's theory.

Starting at step 305, new input requirements are received via the operator interface. Once received, in some embodiments, pre-processing is performed on the requirements to prepare them for use with the learning model. For example, in one embodiment, natural language processing is used to derive input parameters for the learning model based on the new input requirements. Additionally (or alternatively), a feature extraction model may be applied to refine the input parameters for the learning model based on the requirements.

Steps 310-315 represent the assimilation process. At step 310, the intelligent medical imaging scanner determines whether the learning model may be used to generate a configuration of the image scanner corresponding to the new input requirements. If the configuration can be generated, the intelligent medical imaging scanner uses the configuration at step 315 to acquire one or more images of a patient using the image scanner.

If the configuration of the image scanner cannot be generated based on the new input requirements, an accommodation process is performed steps 320 and 325. At step 320, the learning model is modified to generate a new configuration of the image scanner corresponding to the new input requirements. In some embodiments, the learning model is modified during the accommodation process based on patient or operator feedback to the one or more images previously acquired by the image scanner. Then, at step 325, the new configuration is used to acquire the images of the patient using the image scanner.

In addition, the image acquisition, the intelligent medical imaging scanner may be configured to perform other clinical functions. For example, in one embodiment, the intelligent medical imaging scanner may use one or more models to predict a disease outcome based on the images. In other embodiments, the intelligent medical imaging scanner generates a workflow for the image scanner based on the new configuration of the image scanner. Any operator feedback regarding the workflow may be used during the accommodation process in deriving new configurations. This feedback may be manually input by the operator or, in some instances, automatically detected by the system. For example, in one embodiment, the feedback comprises a modification to the workflow automatically detected by the intelligent medical imaging scanner system while an operator is performing the workflow.

Figure 4:
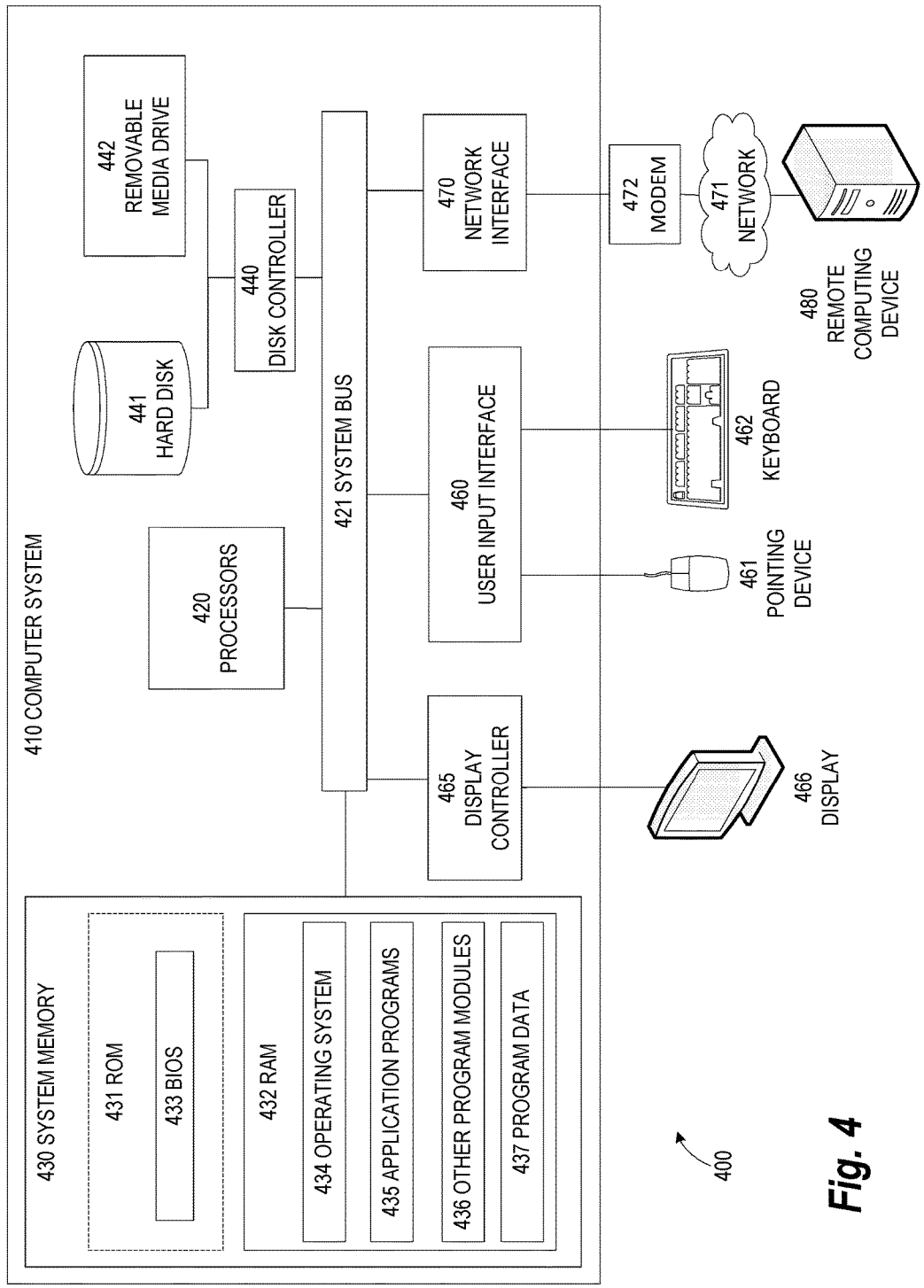
FIG. 4 illustrates an exemplary computing environment.

FIG. 4 illustrates an exemplary computing environment 400 within which embodiments of the invention may be implemented. For example, this computing environment 400 may be used to implement the processes described above with respect to FIGS. 2A, 2B, and 3. In some embodiments, the computing environment 400 may be used to implement one or more of the components illustrated in the system 100 of FIG. 1. The computing environment 400 may include computer system 410, which is one example of a computing system upon which embodiments of the invention may be implemented. Computers and computing environments, such as computer system 410 and computing environment 400, are known to those of skill in the art and thus are described briefly here.

As shown in FIG. 4, the computer system 410 may include a communication mechanism such as a bus 421 or other communication mechanism for communicating information within the computer system 410. The computer system 410 further includes one or more processors 420 coupled with the bus 421 for processing the information. The processors 420 may include one or more central processing units (CPUs), graphical processing units (GPUs), or any other processor known in the art.

The computer system 410 also includes a system memory 430 coupled to the bus 421 for storing information and instructions to be executed by processors 420. The system memory 430 may include computer readable storage media in the form of volatile and/or nonvolatile memory, such as read only memory (ROM) 431 and/or random access memory (RAM) 432. The system memory RAM 432 may include other dynamic storage device(s) (e.g., dynamic RAM, static RAM, and synchronous DRAM). The system memory ROM 431 may include other static storage device (s) (e.g., programmable ROM, erasable PROM, and electrically erasable PROM). In addition, the system memory 430 may be used for storing temporary variables or other intermediate information during the execution of instructions by the processors 420. A basic input/output system (BIOS) 433 containing the basic routines that help to transfer information between elements within computer system 410, such as during start-up, may be stored in ROM 431. RAM 432 may contain data and/or program modules that are immediately accessible to and/or presently being operated on by the processors 420. System memory 430 may additionally include, for example, operating system 434, application programs 435, other program modules 436 and program data 437.

The computer system 410 also includes a disk controller 440 coupled to the bus 421 to control one or more storage devices for storing information and instructions, such as a hard disk 441 and a removable media drive 442 (e.g., floppy disk drive, compact disc drive, tape drive, and/or solid state drive). The storage devices may be added to the computer system 410 using an appropriate device interface (e.g., a small computer system interface (SCSI), integrated device electronics (IDE), Universal Serial Bus (USB), or FireWire).

The computer system 410 may also include a display controller 465 coupled to the bus 421 to control a display 466, such as a cathode ray tube (CRT) or liquid crystal display (LCD), for displaying information to a computer user. The computer system includes a user input interface 460 and one or more input devices, such as a keyboard 462 and a pointing device 461, for interacting with a computer user and providing information to the processors 420. The pointing device 461, for example, may be a mouse, a trackball, or a pointing stick for communicating direction information and command selections to the processors 420 and for controlling cursor movement on the display 466. The display 466 may provide a touch screen interface which allows input to supplement or replace the communication of direction information and command selections by the pointing device 461.

The computer system 410 may perform a portion or all of the processing steps of embodiments of the invention in response to the processors 420 executing one or more sequences of one or more instructions contained in a memory, such as the system memory 430. Such instructions may be read into the system memory 430 from another computer readable medium, such as a hard disk 441 or a removable media drive 442. The hard disk 441 may contain one or more datastores and data files used by embodiments of the present invention. Datastore contents and data files may be encrypted to improve security. The processors 420 may also be employed in a multi-processing arrangement to execute the one or more sequences of instructions contained in system memory 430. In alternative embodiments, hardwired circuitry may be used in place of or in combination with software instructions. Thus, embodiments are not limited to any specific combination of hardware circuitry and software.

As stated above, the computer system 410 may include at least one computer readable medium or memory for holding instructions programmed according to embodiments of the invention and for containing data structures, tables, records, or other data described herein. The term "computer readable medium" as used herein refers to any medium that participates in providing instructions to the processors 420 for execution. A computer readable medium may take many forms including, but not limited to, non-volatile media, volatile media, and transmission media. Non-limiting examples of non-volatile media include optical disks, solid state drives, magnetic disks, and magneto-optical disks, such as hard disk 441 or removable media drive 442. Non-limiting examples of volatile media include dynamic memory, such as system memory 430. Non-limiting examples of transmission media include coaxial cables, copper wire, and fiber optics, including the wires that make up the bus 421. Transmission media may also take the form of acoustic or light waves, such as those generated during radio wave and infrared data communications.

The computing environment 400 may further include the computer system 410 operating in a networked environment using logical connections to one or more remote computers, such as remote computer 480. Remote computer 480 may be a personal computer (laptop or desktop), a mobile device, a server, a router, a network PC, a peer device or other common network node, and typically includes many or all of the elements described above relative to computer system 410. When used in a networking environment, computer system 410 may include modem 472 for establishing communications over a network 471, such as the Internet. Modem 472 may be connected to bus 421 via user network interface 470, or via another appropriate mechanism.

Network 471 may be any network or system generally known in the art, including the Internet, an intranet, a local area network (LAN), a wide area network (WAN), a metropolitan area network (MAN), a direct connection or series of connections, a cellular telephone network, or any other network or medium capable of facilitating communication between computer system 410 and other computers (e.g., remote computer 480). The network 471 may be wired, wireless or a combination thereof. Wired connections may be implemented using Ethernet, Universal Serial Bus (USB), RJ-11 or any other wired connection generally known in the art. Wireless connections may be implemented using Wi-Fi, WiMAX, and Bluetooth, infrared, cellular networks, satellite or any other wireless connection methodology generally known in the art. Additionally, several networks may work alone or in communication with each other to facilitate communication in the network 471.

The embodiments of the present disclosure may be implemented with any combination of hardware and software. In addition, the embodiments of the present disclosure may be included in an article of manufacture (e.g., one or more computer program products) having, for example, computer-readable, non-transitory media. The media has embodied therein, for instance, computer readable program code for providing and facilitating the mechanisms of the embodiments of the present disclosure. The article of manufacture can be included as part of a computer system or sold separately.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

An executable application, as used herein, comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters.

A graphical user interface (GUI), as used herein, comprises one or more display images, generated by a display processor and enabling user interaction with a processor or other device and associated data acquisition and processing functions. The GUI also includes an executable procedure or executable application. The executable procedure or executable application conditions the display processor to generate signals representing the GUI display images. These signals are supplied to a display device which displays the image for viewing by the user. The processor, under control of an executable procedure or executable application, manipulates the GUI display images in response to signals received from the input devices. In this way, the user may interact with the display image using the input devices, enabling user interaction with the processor or other device.

The functions and process steps herein may be performed automatically or wholly or partially in response to user command. An activity (including a step) performed automatically is performed in response to one or more executable instructions or device operation without user direct initiation of the activity.

The system and processes of the figures are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. As described herein, the various systems, subsystems, agents, managers and processes can be implemented using hardware components, software components, and/or combinations thereof. No claim element herein is to be construed under the provisions of 35 U.S.C. 112, sixth paragraph, unless the element is expressly recited using the phrase "means for."

The invention claimed is:

1. An intelligent medical imaging scanner system comprising:
   an image scanner;
   an operator interface configured to receive operator input;
   a database comprising a learning model for relating configurations of the image scanner to operator input requirements;
   one or more processors;
   a non-transitory, computer-readable storage medium in operable communication with the one or more processors, wherein the computer-readable storage medium contains one or more programming instructions that, when executed, cause the processors to:
   in response to receiving of new input requirements via the operator interface, determining whether the learning model may be used to generate a configuration of the image scanner corresponding to the new input requirements,
if the configuration of the image scanner can be generated based on the new input requirements, using the configuration to acquire one or more images of a patient using the image scanner, and
if the configuration of the image scanner cannot be generated based on the new input requirements, performing an accommodation process comprising (a) modifying the learning model to generate a new configuration of the image scanner corresponding to the new input requirements and based on at least patient or operator feedback to the one or more images acquired by the image scanner, and (b) using the new configuration to acquire the one or more images of the patient using the image scanner.

2. The intelligent medical imaging scanner system of claim 1, wherein the computer-readable storage medium further comprises additional programming instructions that, when executed, cause the processors to:
use natural language processing to derive input parameters for the learning model based on the new input requirements received via the operator interface; and
apply a feature extraction model to refine the input parameters for the learning model based on the new input requirements.

3. The intelligent medical imaging scanner system of claim 1, wherein the computer-readable storage medium further comprises additional programming instructions that, when executed, cause the processors to:
predict a disease outcome based on the one or more images.

4. The intelligent medical imaging scanner system of claim 1, wherein the learning model is modified during the accommodation process based on patient feedback to the one or more images acquired by the image scanner.

5. The intelligent medical imaging scanner system of claim 1, wherein applying the new configuration to acquire the one or more images of the patient using the image scanner comprises:
deriving a workflow for the image scanner based on the new configuration of the image scanner.

6. The intelligent medical imaging scanner system of claim 5, wherein the operator interface configured to receive operator feedback related to the workflow for the image scanner and wherein the learning model is modified based on the operator feedback.

7. The intelligent medical imaging scanner system of claim 6, wherein the operator feedback comprises a modification to the workflow automatically detected by the intelligent medical imaging scanner system while an operator is performing the workflow.

8. A computer-implemented method for performing medical image acquisition, the method comprising:
in response to receiving input requirements via an operator interface of an image scanner, determining whether one or more learning models may be used to generate a configuration of the image scanner corresponding to the input requirements;
if the configuration of the image scanner can be generated based on the input requirements, generating the configuration with the learning models based on the input requirements;
if the configuration of the image scanner cannot be generated based on the input requirements, modifying the learning models to generate the configuration of the image scanner corresponding to the input requirements and based on at least patient or operator feedback to the one or more images acquired by the image scanner; and
applying the configuration to acquire one or more images of a patient using the image scanner.

9. The method of claim 8, further comprising:
using natural language processing to extract scanner-related features from the input requirements,
wherein the scanner-related features are used by learning models in deriving the configuration.

10. The method of claim 8, where the configuration comprises one or more of recommended acquisition parameters, recommended workflow, recommended image processing parameters, and recommended image processing algorithms.

11. The method of claim 10, wherein the one or more learning models comprise a deep learning artificial neural network.

12. The method of claim 10, further comprising:
receiving feedback comprising an operator modification to one or more of the recommended acquisition parameters, the recommended workflow, and the recommended image processing parameters, or the recommended image processing algorithms; and
updating the one or more learning models based on the feedback.

13. The method of claim 10, wherein the one or more learning models comprise:
a first model configured to derive the recommended acquisition parameters based on the input requirements,
a second model configured to derive the recommended workflow based on the input requirements,
a third model configured to derive the recommended image processing parameters and the recommended image processing algorithms based on the input requirements.

14. The method of claim 13, comprising:
receiving first feedback comprising an operator modification to the recommended acquisition parameters; and
modifying the first model based on the first feedback.

15. The method of claim 14, wherein the second model is configured to derive the recommended workflow based on the input requirements as modified in the first feedback.

16. The method of claim 15, comprising:
receiving second feedback comprising an operator modification to the recommended workflow; and
modifying the second model based on the second feedback.

17. The method of claim 16, wherein the third model is configured to derive the recommended image processing parameters and the recommended image processing algorithms based on the input requirements as modified in the first feedback and the second feedback.

18. The method of claim 17, comprising:
receiving third feedback comprising an operator modification to the recommended workflow; and
modifying the third model based on the third feedback.

19. A computer-implemented method for configuring an intelligent medical scanner, the method comprising:
receiving input requirements corresponding to a medical imaging scan of a patient;
processing the input requirements with a learning model to determine whether a pre-existing configuration of the intelligent medical scanner exists which is compatible with the input requirements; and
if the pre-existing configuration does not exist, (a) collecting operator feedback to one or more previous image acquisitions performed using the intelligent medical scanner and (b) modifying the learning model based on the operator feedback to generate a new configuration based on the input requirements and based on at least patient or operator feedback to the one or more images acquired by the image scanner.

\* \* \* \* \*